(12) United States Patent
Pryor

(10) Patent No.: US 6,364,161 B1
(45) Date of Patent: Apr. 2, 2002

(54) OXYGEN CONSERVER

(75) Inventor: David A. Pryor, Denton, TX (US)

(73) Assignee: Victor Equipment Company, St. Louis, MO (US)

( * ) Notice: Subject to any disclaimer, the term of this patent is extended or adjusted under 35 U.S.C. 154(b) by 0 days.

(21) Appl. No.: 09/671,789

(22) Filed: Sep. 27, 2000

(51) Int. Cl.[7] ................................................. A62B 9/02
(52) U.S. Cl. .................. 222/3; 128/204.26; 128/205.24
(58) Field of Search .......................... 222/3; 128/204.26, 128/204.27, 205.24

(56) References Cited

U.S. PATENT DOCUMENTS

| | | |
|---|---|---|
| 2,318,827 A | 5/1943 | Yant |
| 2,552,595 A | 5/1951 | Seeler |
| 3,285,261 A | 11/1966 | Chaney |
| 3,400,713 A | 9/1968 | Finan |
| 3,434,471 A | 3/1969 | Liston |
| 3,524,464 A | 8/1970 | Glidden |
| 3,776,422 A | 12/1973 | Wise |
| 3,783,891 A | 1/1974 | Christianson |
| 3,795,257 A * | 3/1974 | Fabish et al. ................ 137/491 |
| 3,815,593 A | 6/1974 | Baumont |

(List continued on next page.)

FOREIGN PATENT DOCUMENTS

WO    WO 87/02590    5/1987

OTHER PUBLICATIONS

Ohmeda advertisement entitled, "Ohmeda/Pulse Oximeter", published prior to Aug. 19, 1997.
DeVILBISS advertisement entitled, "Pulse/Dose", copyrighted 1994.
Pulsair, Inc. advertisement entitled, "Pulsair Walkabout", copyrighted 1991.
Perry Oxygen Systems Inc . advertisement entitled, "Pulsed Oxygen On Demand", published prior to Aug. 19, 1997.
Pulsair technical memorandum entitled, "Pulsair® Oxygen Delivery System", copyrighted 1990.

(List continued on next page.)

*Primary Examiner*—J. Casimer Jacyna
(74) *Attorney, Agent, or Firm*—Senniger, Powers, Leavitt & Roedel

(57) ABSTRACT

A pneumatic oxygen conserver for providing oxygen to a patient. The conserver includes a body having a cavity and a main diaphragm dividing the cavity into first and second chambers. A first inlet passage delivers oxygen from an oxygen supply to the first chamber, and a second inlet passage delivers oxygen from the supply to the second chamber. An outlet passage delivers oxygen from the first chamber to the patient. The main diaphragm is movable between a closed position to prevent oxygen flow through the outlet passage and an open position to permit such flow. Vent passaging vents the second chamber. A pressure sensitive valve is connectable to the patient for permitting flow through the vent passaging when the patient inhales and preventing flow through the vent passaging when the patient exhales. Valving along the second inlet passage moves between an open position to permit flow through the second inlet passage to pressurize the second chamber and enable the conserver to operate in an oxygen conserving mode and a closed position to prevent flow through the second inlet passage, vent the second chamber, and enable the conserver to operate in a continuous flow mode. In the oxygen conserving mode, oxygen is delivered to the patient when the patient inhales, and oxygen flow is prevented through the outlet passage when the patient exhales. When the valving is in the continuous flow mode, oxygen is continuously delivered through the outlet passage.

23 Claims, 6 Drawing Sheets

U.S. PATENT DOCUMENTS

| | | |
|---|---|---|
| 4,054,133 A | 10/1977 | Myers |
| 4,060,078 A | 11/1977 | Bird |
| 4,076,041 A | 2/1978 | Christianson |
| 4,127,123 A | 11/1978 | Bird |
| 4,253,455 A | 3/1981 | Netteland |
| 4,269,216 A | 5/1981 | Sullivan et al. |
| 4,278,110 A | 7/1981 | Price et al. |
| 4,340,045 A | 7/1982 | Manley |
| 4,374,521 A | 2/1983 | Nelson et al. |
| 4,381,002 A | 4/1983 | Mon |
| 4,461,293 A | 7/1984 | Chen |
| 4,462,398 A | 7/1984 | Durkan et al. |
| 4,567,888 A | 2/1986 | Robert et al. |
| 4,575,042 A | 3/1986 | Grimland et al. |
| 4,611,591 A | 9/1986 | Inui et al. |
| 4,612,928 A | 9/1986 | Tiep et al. |
| 4,651,731 A | 3/1987 | Vicenzi et al. |
| 4,665,911 A | 5/1987 | Williams et al. |
| 4,667,670 A | 5/1987 | Feathers |
| 4,681,099 A | 7/1987 | Sato et al. |
| 4,705,034 A | 11/1987 | Perkins |
| 4,706,664 A | 11/1987 | Snook et al. |
| 4,744,356 A | 5/1988 | Greenwood |
| 4,784,130 A | 11/1988 | Kenyon et al. |
| 4,823,788 A | 4/1989 | Smith et al. |
| 4,848,332 A | 7/1989 | Champain |
| 4,856,507 A | 8/1989 | Ouillon et al. |
| 4,858,606 A | 8/1989 | Hamilin |
| 4,873,971 A | 10/1989 | Perkins |
| 4,898,174 A | 2/1990 | Fangrow, Jr. |
| 4,928,684 A | 5/1990 | Breitenfelder et al. |
| 4,932,401 A | 6/1990 | Perkins |
| 4,932,402 A | 6/1990 | Snook et al. |
| 4,971,049 A | 11/1990 | Rotariu et al. |
| 4,986,269 A | 1/1991 | Hakkinen |
| 5,002,050 A | 3/1991 | McGinnis |
| 5,005,570 A | 4/1991 | Perkins |
| 5,016,626 A | 5/1991 | Jones |
| 5,024,219 A | 6/1991 | Dietz |
| 5,038,770 A | 8/1991 | Perkins |
| 5,038,771 A | 8/1991 | Dietz |
| 5,048,515 A | 9/1991 | Sanso |
| 5,074,299 A | 12/1991 | Dietz |
| 5,165,397 A | 11/1992 | Arp |
| 5,247,926 A | 9/1993 | Harral |
| 5,275,153 A | 1/1994 | Kay |
| 5,348,001 A | 9/1994 | Danon |
| 5,357,950 A | 10/1994 | Wippler et al. |
| 5,360,000 A | 11/1994 | Carter |
| 5,370,112 A | 12/1994 | Perkins |
| 5,386,824 A | 2/1995 | Nelepka |
| 5,390,666 A | 2/1995 | Kimm et al. |
| 5,464,009 A | 11/1995 | Tatarek-Gintowt |
| 5,603,315 A | 2/1997 | Sasso, Jr. |
| 5,632,298 A | 5/1997 | Artinian |
| 5,685,296 A | 11/1997 | Zdrojkowski et al. |
| 5,685,297 A | 11/1997 | Schuler |
| 5,687,712 A | 11/1997 | Semeia |
| 5,701,889 A | 12/1997 | Danon |
| 5,720,276 A | 2/1998 | Kobatake et al. |
| 5,738,088 A | 4/1998 | Townsend |
| 5,787,882 A | 8/1998 | Hamilton |
| 5,839,436 A | 11/1998 | Fangrow, Jr. et al. |
| 5,881,725 A | 3/1999 | Hoffman et al. |
| 5,911,220 A | 6/1999 | Morgan et al. |
| 5,937,855 A | 8/1999 | Zdrojkowski et al. |
| 6,116,242 A * | 9/2000 | Frye et al. ............. 128/205.24 |

OTHER PUBLICATIONS

Puritan Bennett advertisement entitled, "It All Adds Up . . . ", published prior to Aug. 19, 1997.

CHAD Therapeutics advertisement entitled, "Not all home oxygen patients should be homebodies . . . ", published prior to Aug. 19, 1997.

DeVILBISS advertisement entitled, "Is There A Hole In Your Portable Oxygen Program?", published prior to Aug. 19, 1997.

CHAD Therapeutics advertisement entitled, "The Smallest & Lightest Oxygen System Available", copyrighted 1994.

* cited by examiner

OXYGEN CONSERVER

BACKGROUND OF THE INVENTION

This invention relates generally to oxygen delivery systems, and more particularly to a pneumatically controlled oxygen conserver for providing oxygen on demand (i.e., upon inhalation).

Oxygen delivery systems of the type used by patients with pulmonary emphysema, for example, include a source of oxygen (e.g., an oxygen bottle) for holding a supply of oxygen at pressures of up to about 3000 pounds per square inch gauge (psig), a regulator system for reducing the pressure of the oxygen to a pressure suitable for breathing, and a cannula for delivering oxygen to the patient. To increase the life of the oxygen supply, oxygen conservers are frequently used. These devices interrupt the flow of oxygen to the patient, either in response to exhalation, or at timed intervals, thereby reducing the rate of oxygen consumption.

Conservers are generally of two types, those which operate electronically and those which operate pneumatically. Electronic conservers require a power source (e.g., batteries) for operation, thus necessitating periodic replacement or recharging of the power source. The remaining life of the power source, which patients must take into consideration, can be uncertain. Pneumatic conservers, on the other hand, are operated by the inhalation and exhalation of the patient. They require no power source and thus have a significant advantage over electronic conservers. The pneumatic conserver responds to changes in pressure in the cannula to provide oxygen to the patient during inhalation, and to interrupt the flow of oxygen to the patient during exhalation (when oxygen is not needed). However, typical conventional pneumatic conservers are relatively complex in design, requiring a series of spring-activated diaphragms and the like, to ensure oxygen is promptly delivered when the patient inhales and promptly interrupted when the patient exhales.

Some prior oxygen conservers are selectively operable in two modes, an oxygen conserving mode and a continuous flow mode. In the oxygen conserving mode, oxygen is supplied to the patient on an interrupted basis, as described above. In the continuous flow mode, a continuous stream of oxygen is provided to the patient during both inhalation and exhalation. (Continuous delivery during the entire breathing cycle is not necessary for health reasons, but some patients prefer uninterrupted flow.) Typically, when conventional conservers are switched to the continuous flow mode, they do not continuously deliver oxygen until after the patient inhales for the first time. For patients who prefer continuous flow, this can be disconcerting.

There is a need, therefore, for a pneumatic oxygen conserver which overcomes the disadvantages of prior systems.

SUMMARY OF THE INVENTION

Among the several objects of this invention may be noted the provision of a pneumatic oxygen conserver which is selectively operable in either an oxygen conserving mode or in a continuous flow mode, and which is equipped for adjustment of the oxygen flow rate in both modes; the provision of such a conserver which is durable and reliable in operation; the provision of a conserver which quickly delivers oxygen upon inhalation and quickly stops delivery upon exhalation; and the provision of a conserver which begins flow of oxygen prior to inhalation in the continuous flow mode.

Briefly, apparatus of this invention is a pneumatic oxygen conserver for providing oxygen to a patient. The conserver includes a body having a cavity and a main diaphragm dividing the cavity into first and second chambers. A first inlet passage delivers oxygen from an oxygen supply to the first chamber, and a second inlet passage delivers oxygen from the supply to the second chamber. An outlet passage delivers oxygen from the first chamber to the patient. The main diaphragm is movable between a closed position to prevent oxygen flow through the outlet passage and an open position to permit such flow. Vent passaging vents the second chamber. A pressure sensitive valve is connectable to the patient for permitting flow through the vent passaging when the patient inhales and preventing flow through the vent passaging when the patient exhales. Valving along the second inlet passage moves between an open position to permit flow through the second inlet passage to pressurize the second chamber and enable the conserver to operate in an oxygen conserving mode and a closed position to prevent flow through the second inlet passage, vent the second chamber, and enable the conserver to operate in a continuous flow mode. In the oxygen conserving mode, oxygen is delivered to the patient when the patient inhales, and oxygen flow is prevented through the outlet passage when the patient exhales. When the valving is in the continuous flow mode, oxygen is continuously delivered through the outlet passage.

In another aspect of the invention, the conserver comprises, a body, a main diaphragm, a first inlet passage, a second inlet passage and an outlet passage. In addition, the conserver includes a metering orifice positioned along the second inlet passage for restricting flow of oxygen. The conserver also includes a sensing diaphragm extending across a second cavity in the body, dividing the second cavity into third and fourth chambers. A control passage extends through the body connecting the second and third chambers, and a control orifice positioned along the control passage restricts flow of oxygen through the control passage. The sensing diaphragm is movable between a closed position in which flow through the control passage is prevented and an open position in which such flow is permitted. A sensing passage extending through the body to the fourth chamber is adapted for connection to the patient so pressure in the fourth chamber decreases when the patient inhales and increases when the patient exhales. Further, the conserver includes a vent passage extending through the body from the third chamber for venting the third chamber. The sensing diaphragm moves to its open position when pressure in the fourth chamber decreases as the patient inhales to vent the second and third chambers and to move the main diaphragm to its open position to deliver oxygen through the outlet passage to the patient, and the sensing diaphragm moves to its closed position when pressure in the fourth chamber increases as the patient exhales to pressurize the second chamber and to move the main diaphragm to its closed position to prevent flow of oxygen to the patient. The vent passage is sized sufficiently large that the sensing diaphragm moves to its closed position in less than about 500 milliseconds after pressure in the fourth chamber approaches about 22 psig as the patient exhales, and the vent passage is sized sufficiently small that the sensing diaphragm moves to its open position in less than about 500 milliseconds after pressure in the fourth chamber falls below about 21 psig as the patient inhales.

Other objects and features of the present invention will be in part apparent and in part pointed out hereinafter.

BRIEF DESCRIPTION OF THE DRAWINGS

Corresponding reference characters indicate corresponding parts throughout the several views of the drawings.

DETAILED DESCRIPTION OF THE PREFERRED EMBODIMENT

Figure 1:
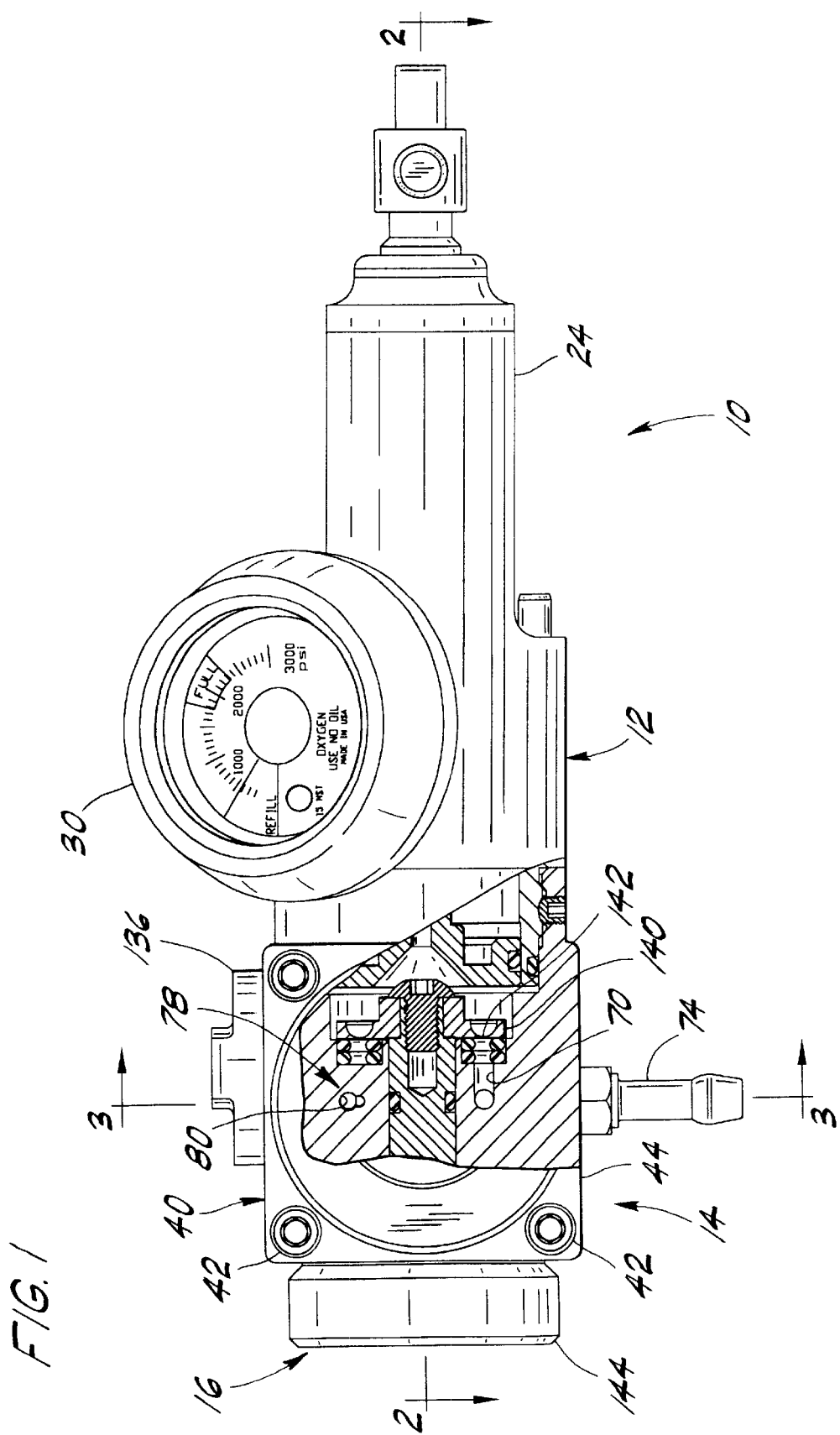
FIG. 1 is a side elevation in partial section of a pneumatic oxygen conserver of the present invention.

Referring now to the drawings and in particular to FIG. 1, an oxygen conserver/regulator unit of the present invention is designated in its entirety by the reference number 10. The unit 10 comprises a conventional regulator (generally designated by 12), a pneumatic oxygen conserver (generally designated by 14), and a flow control mechanism (generally designated by 16).

Figure 2:
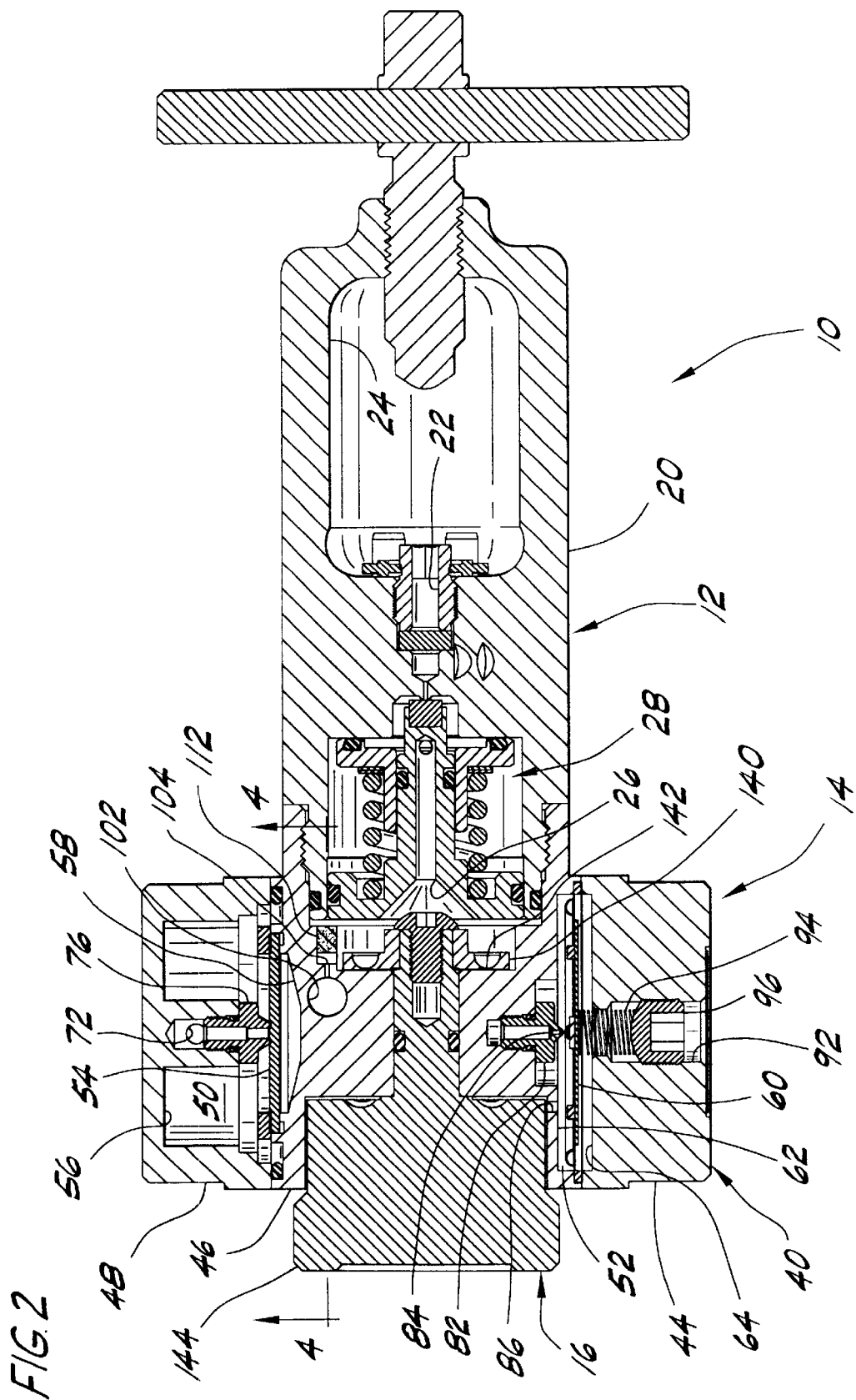
FIG. 2 is cross section of the conserver taken in the plane of line 2—2 of FIG. 1.

As illustrated in FIG. 2, the regulator 12 comprises a regulator body 20 having an inlet 22 adapted for connection to a bottle (not shown) by means of a yoke 24, the construction and operation of which all are known in the art. One such yoke 24 is described in U.S. Pat. No. 5,704,589, issued Jan. 6, 1998. The regulator body 20 also has an outlet 26. A pressure regulating mechanism, generally designated by 28, of conventional design is provided in the regulator body 20. This mechanism 28 is operable to receive oxygen from the inlet 22 at a first pressure (e.g., 2000 psig corresponding to the bottle pressure) and to reduce the pressure of the oxygen to a second lower pressure (e.g., 22 psig) for delivery to the outlet 26 of the regulator 20. A regulator suitable for use may be obtained from Victor Equipment Company located in Denton, Tex. One such regulator 20 is described in the U.S. Pat. No. 4,679,584, issued Jul. 14, 1987. As illustrated in FIG. 1, the regulator 20 includes a pressure gauge 30 with a dial for monitoring the supply of oxygen in the bottle.

The construction of the conserver 14 is shown in FIGS. 1–5. As illustrated in FIG. 2, the conserver 14 comprises a body, generally designated by 40, made of suitable material (e.g., aluminum) fabricated from a plurality of separate parts secured by fasteners 42 (FIG. 1) to form a unitary assembly. In the preferred embodiment shown in the drawings, the body 40 includes three blocks, identified for convenience as a sensor block 44, an inlet block 46 mounted adjacent the sensor block, and an outlet block 48. The conserver body 40 is securely fastened to the regulator body 20 with screw fasteners (not shown).

As further illustrated in FIG. 2, the conserver body 40 is formed with a first cavity 50 defined by recesses in the outlet block 48 and inlet block 46, and a second cavity 52 defined by recesses in the inlet block 46 and sensor block 44. A main diaphragm 54 extends across the first cavity 50 and divides it into first and second chambers 56, 58, respectively, on opposite sides of the diaphragm. A sensing or pilot diaphragm 60 extends across the second cavity 52 and divides it into third and fourth chambers 62, 64, respectively, on opposite sides of the diaphragm.

Figure 3:
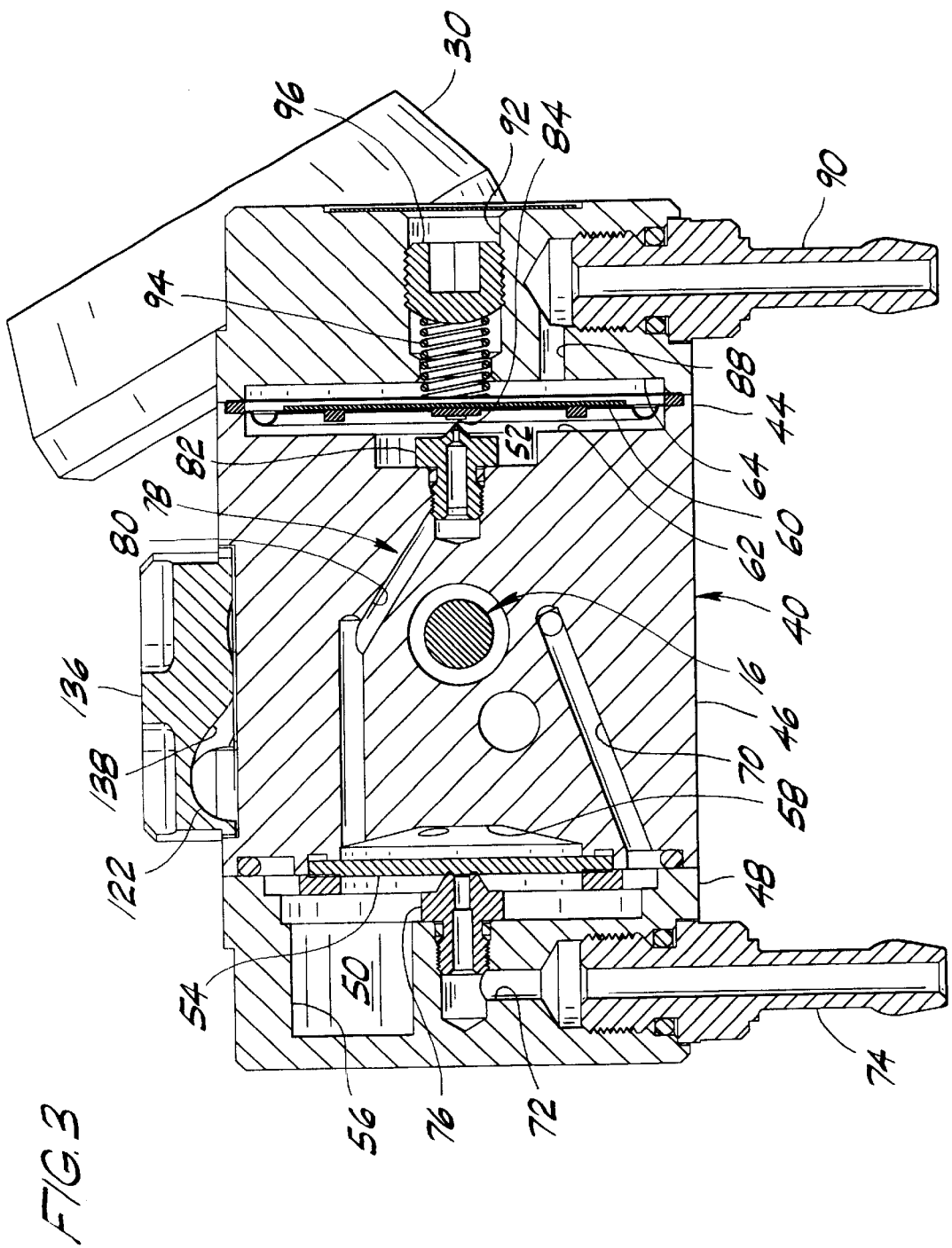
FIG. 3 is cross section of the conserver taken in the plane of line 3—3 of FIG. 1.

As illustrated in FIGS. 1 and 3, a first inlet passage 70 extends through the conserver body 40 to the first chamber 56 for delivering oxygen from the oxygen supply to the first chamber. As further illustrated in FIG. 3, an outlet passage 72 extends through the conserver body 40 from the first chamber 56 for delivering oxygen from the first chamber to the patient. The outlet passage 72 includes a tubing nipple 74 adapted for connection to one end of a conventional dual tube cannula (not shown). The passage 72 also includes a seat 76 positioned in the first chamber 56 adjacent the main diaphragm 54 so the main diaphragm can move between a closed position in which it sealingly engages the seat to prevent flow of oxygen through the outlet passage 72 and an open position in which it disengages the seat so flow is permitted. The main diaphragm 54 is resiliently flexible and biased toward its closed position.

Vent passaging, generally designated by 78 in FIG. 3, extends through the body 40 from the second chamber 58 for venting oxygen from the second chamber. The vent passaging 78 includes a control passage 80 extending through the conserver body 40 connecting the second chamber 58 and third chamber 62 for delivering oxygen from the second chamber to the third chamber. A control nozzle 82 having a control orifice 84 is positioned along the control passage 80 for restricting oxygen flow through the passage. The nozzle 82 is positioned along the vent passaging 78 adjacent the sensing diaphragm 60 so the sensing diaphragm can move between a closed position in which it sealingly engages the nozzle to prevent flow through the nozzle and the control passage 80, and an open position in which it disengages the nozzle to permit flow through the control orifice 84. The sensing diaphragm 60 is resiliently flexible and biased toward its closed position. When the sensing diaphragm 60 is open permitting flow through the control orifice 84, oxygen enters the third chamber 62 through the nozzle 82. As illustrated in FIG. 3, the vent passaging 78 includes a vent passage opening 86 extending through the body 40 from the third chamber 62 to maintain the third chamber approximately at ambient pressure. Thus, when the sensing diaphragm 60 is open, the second chamber 58 vents into the third chamber 62 through the vent passaging 78 and approaches ambient pressure. As will be appreciated by those skilled in the art, the sensing diaphragm 60 and nozzle 82 form a pressure sensitive valve which controls flow through the vent passaging 78.

As shown in FIG. 3, a sensing passage 88 extends through the conserver body 40 from the fourth chamber 64 for sensing inhalation and exhalation of the patient. Pressure in the fourth chamber 64 decreases when the patient inhales and increases when the patient exhales. The passage 88 includes a tubing nipple 90 adapted for connection to an end of the conventional dual tube cannula opposite the end connected to the outlet nipple 74. Thus, the pressure sensitive valve formed by the sensing diaphragm 60 and the nozzle 82 is operatively connectable to the patient for permitting flow through the vent passaging 78 when the patient inhales and for preventing flow through the vent passaging when the patient exhales.

As illustrated in FIG. 3, a threaded hole 92 extends from the second cavity 52. The hole 92 is co-axial with the sensing diaphragm 60 and sized for receiving a coil spring 94 which biases the sensing diaphragm toward its closed position. A threaded set screw 96 engages the spring 94. The set screw 96 may be adjusted to change the spring compression for adjusting the sensitivity of the pressure sensitive valve.

Figure 4:
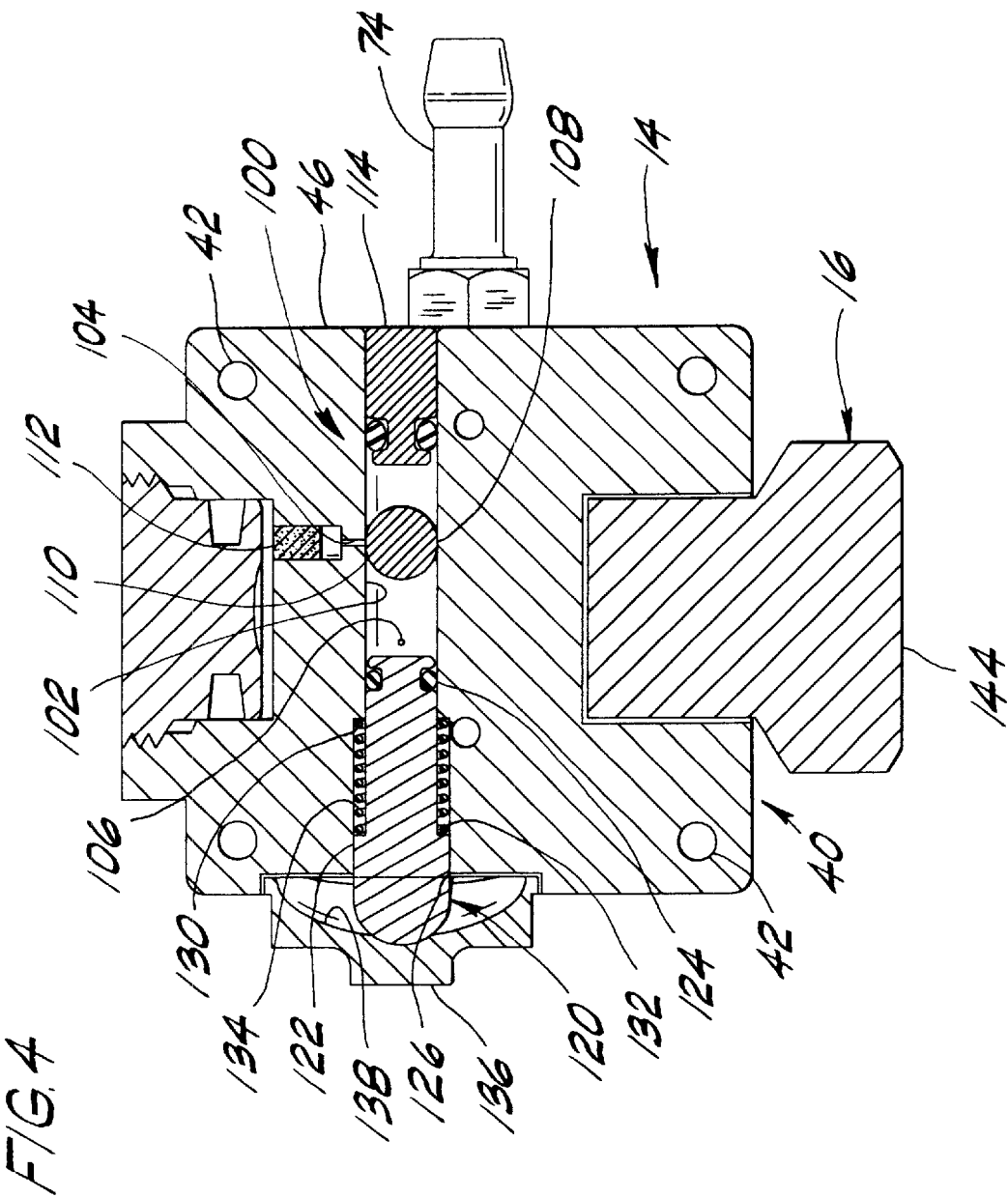
FIG. 4 is cross section of the conserver taken in the plane of line 4—4 of FIG. 2.

As shown in FIG. 4, a second inlet passage, generally designated by 100, extends through the conserver body 40 to the second chamber 58 (FIG. 3) for delivering oxygen from the supply to the second chamber.

Figure 5:
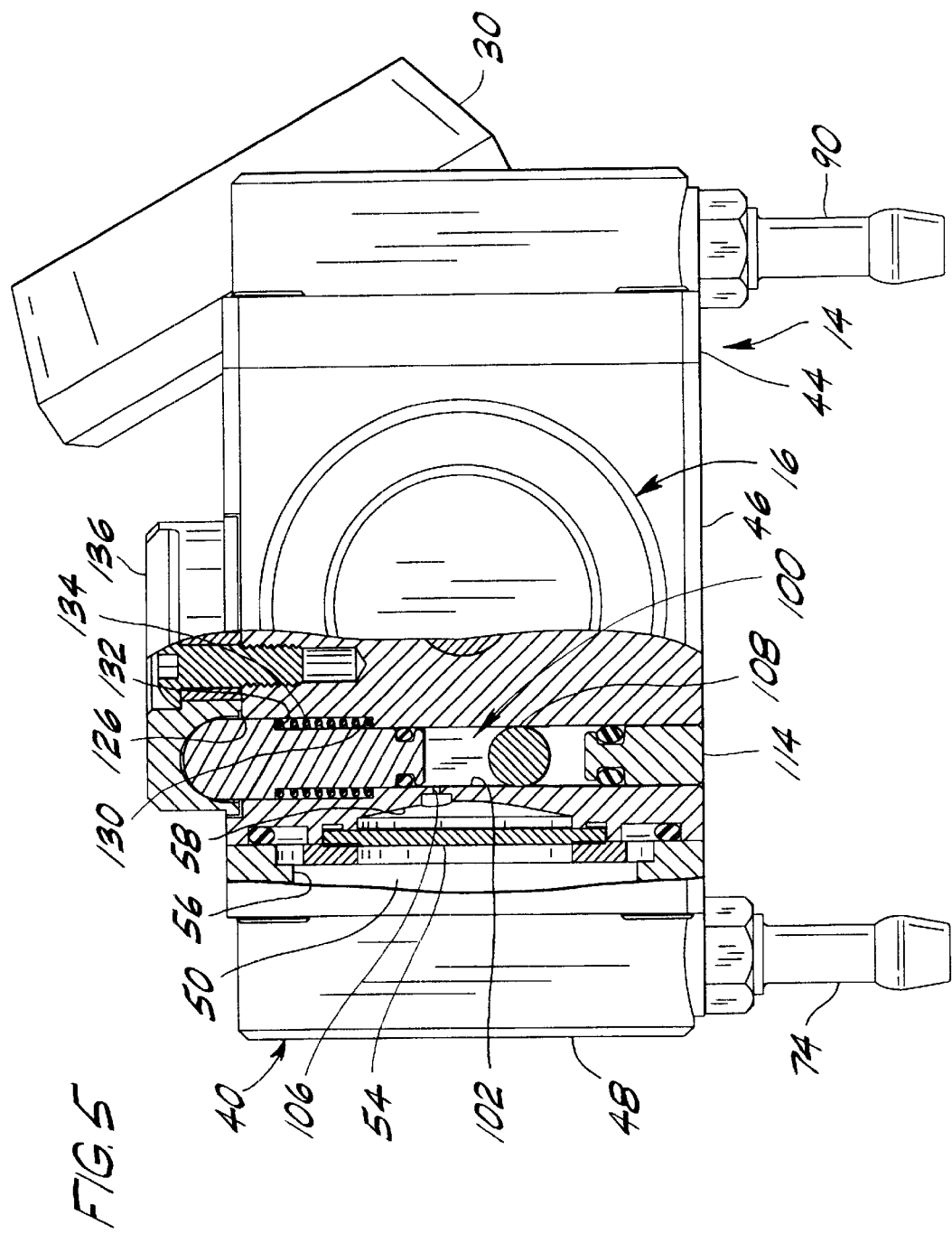
FIG. 5 is an end view of the conserver in partial section.

The second inlet passage 100 includes an elongate hole 102 extending through the body 40 having an inlet passageway 104 extending into the hole and an outlet passageway 106 extending from the hole at a position longitudinally offset from the inlet passageway. As will be explained in further detail below, the inlet passageway 104 communicates with the oxygen supply to deliver oxygen to the hole 102. Further, as shown in FIG. 5 the outlet passageway 106 connects the hole 102 to the second chamber 58 for delivering oxygen from the hole to the second chamber. A spherical plug 108 positioned in the hole 102 partially blocks flow through an outlet 110 of the inlet passageway 104 to create a conventional adjustable metering orifice for metering flow through the second inlet passage 100. A sintered metal filter 112 positioned along the second inlet passage 100 upstream from the outlet 110 prevents the metering orifice from becoming blocked with debris. As will be appreciated by those skilled in the art, flow through the second inlet passage 100 can be adjusted when the conserver 10 is assembled by adjusting the position of the plug 108 with respect to the outlet 110. The plug 108 is held in position by a press fit with the hole 102. Adjustable orifices of this type are known in the art as evidenced by U.S. Pat. No. 4,366,947, issued Jan. 4, 1983. Once the plug 108 is positioned to provide the desired orifice flow, a cover 114 is positioned in the hole 102.

Again referring to FIG. 4, a valve, generally designated by 120, is slidably positioned in the hole 102 near the outlet passageway 106. The valve 120 includes a body 122 having an O-ring seal 124 which may be selectively positioned on an upstream side of the outlet passageway 106 or on a downstream side of the outlet passageway as shown in FIG. 4. When the valve body 122 is positioned so the seal 124 is positioned upstream from the outlet passageway 104 between the inlet passageway and the outlet passageway 106, the seal is said to be in a continuous flow position. In this position, the seal 124 blocks flow through the hole 102 from the oxygen supply to the second chamber 58, and the second chamber 58 continuously vents through the outlet passageway 106 and an open end 126 of the hole 102 opposite the cover 114 so the second chamber remains at ambient pressure. The diameter of the valve body 122 is less than the diameter of the hole 102 so oxygen is free to pass through an annular clearance opening formed between the body and the hole. Although the annular clearance opening may have other areas without departing from the scope of the present invention, in one embodiment the opening has an area of about 0.0004 square inches. When the valve body 122 is positioned so the seal 124 is between the outlet passageway 106 and the end 126 of the hole 102, the seal is said to be in a conserving flow position. In this position, the seal blocks flow through the end of the hole to prevent the second chamber 58 from venting, but allows oxygen to flow from the oxygen supply to the second chamber 58 to pressurize the second chamber.

Figure 6:
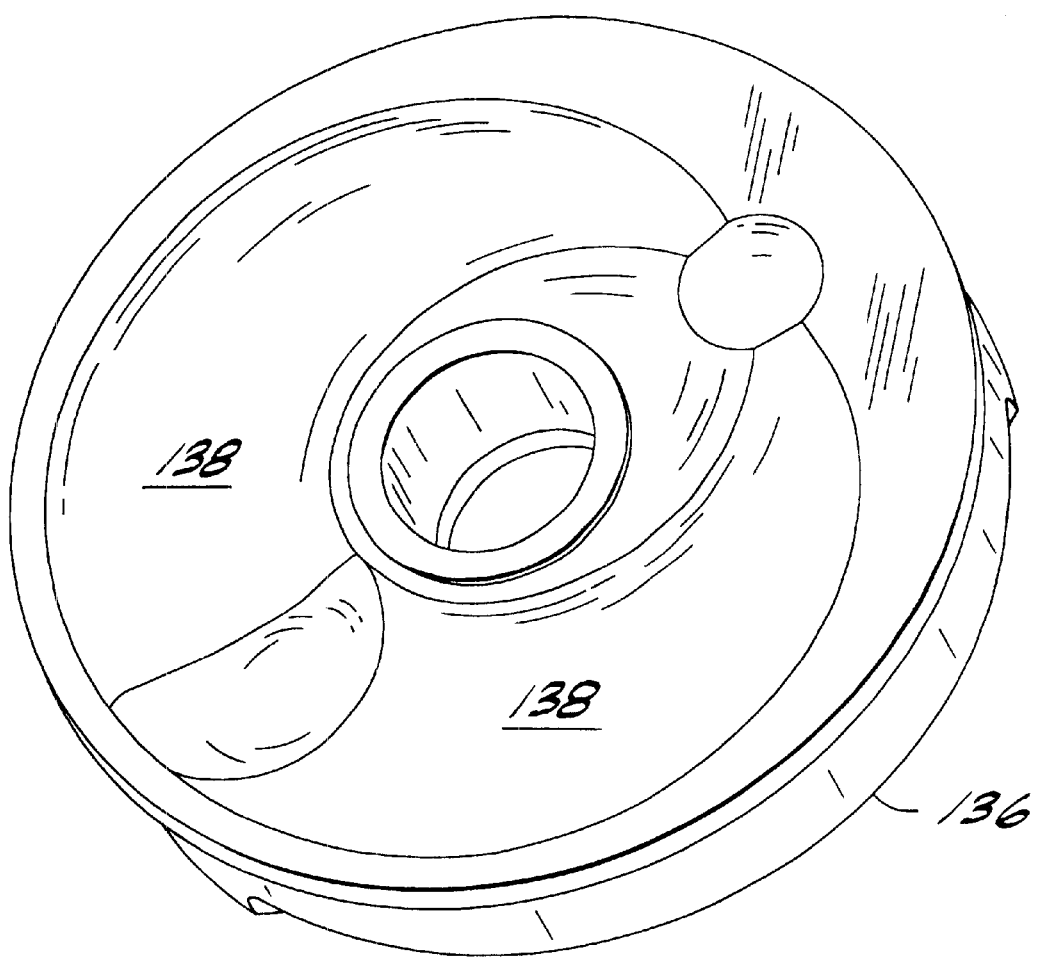
FIG. 6 is a perspective of a mode selector knob of the conserver.

As illustrated in FIG. 4, the hole 102 and valve body 122 include facing shoulders 130, 132, respectively, which engage a coil spring 134 to bias the valve body toward the conserving flow position. A mode selector knob 136 is rotatably mounted on the conserver body 40 adjacent the hole 102. As illustrated in FIG. 6, a face of the knob 136 facing the conserver body 40 includes a cam surface 138 which engages the valve body 122. As the knob 136 rotates, the cam surface 138 positions the valve body 122 within the hole 102 and selectively moves the seal 124 between the conserving flow position and the continuous flow position.

As illustrated in FIG. 1, the flow control mechanism 16 includes an orifice plate 140 rotatably mounted on the body 40. The plate 140 has several differently sized orifices 142 spaced at intervals around the plate. The plate 140 is rotatable to selectively align one of the orifices 142 with the first inlet passage 70 to deliver oxygen through the inlet passage at a selected flow rate. A knob 144 is connected to the orifice plate to align the selected orifice with the inlet passage 70. Since the mechanism 16 is conventional in all other respects, it will not be described in further detail.

Although the vent passaging 78 may have other sizes without departing from the scope of the present invention, the passaging, and more particularly the vent opening 86, of one preferred embodiment is sized sufficiently large that the sensing diaphragm 60 moves to its closed position in less than about 500 milliseconds after pressure in the fourth chamber 64 approaches about 22 psig as the patient exhales. Moreover, the vent passage opening 86 is sized sufficiently small that the sensing diaphragm 60 moves to its open position in less than about 500 milliseconds after pressure in the fourth chamber 64 falls below about 22 psig as the patient inhales. In addition, although the vent passaging 78 may have other sizes without departing from the scope of the present invention, in one embodiment, the vent passage opening 86 has a minimum effective flow area which is about 3400 percent of the minimum effective flow area of the control orifice 84. Still further, the vent passage opening 86 has a minimum effective flow area of about 0.0017 square inches and the control orifice 84 has a minimum effective flow area of about 0.00005 square inches.

When the seal 124 (FIG. 4) is positioned in the conserving flow position between the inlet passageway 104 and the outlet passageway 106, the conserver 10 operates in an oxygen conserving mode. As the patient inhales in this mode, pressure in the fourth chamber 64 drops and the pressure sensitive valve formed by the sensing diaphragm 60 and the nozzle opens to permit flow through the vent passaging 78 to vent the second chamber 58. When the second chamber 58 vents, the main diaphragm 54 moves to its open position and delivers oxygen through the outlet passage 72 to the patient. As the patient exhales, pressure in the fourth chamber 64 rises and the pressure sensitive valve closes and prevents flow through the vent passaging 78 to pressurize the second chamber 58. When the second chamber 58 pressurizes, the main diaphragm 54 moves to its closed position for preventing oxygen flow through the outlet passage 72 to the patient. Thus, oxygen flows to the patient during inhalation and stops during exhalation.

When the seal 124 is positioned in the continuous flow position between the outlet passageway 106 and the end 126 of the hole 102, the conserver 10 is said to be in a continuous flow mode. In this mode, the second chamber 58 vents through the pressure sensitive valving causing the main diaphragm 54 to move to its open position to deliver oxygen continuously through the outlet passage 72 to the patient both during inhalation and exhalation. Moreover, when the valve 120 is switched to the continuous flow, the second chamber 58 immediately depressurizes to ambient pressure through the open end 126 of the hole 102. Thus, the main diaphragm 54 immediately moves to its open position. In some prior art conservers, the patient had to inhale before the oxygen began to flow.

It will be apparent from the foregoing that the conserver of the present invention has many advantages. Because the conserver is pneumatic, it does not require a power source. Further, the conserver is operable in both "oxygen conserving" and "continuous flow" modes, and the flow rate is adjustable in both modes via flow control mechanism 16. Also, in the "oxygen conserving mode", the conserver operates on demand to provide oxygen as it is needed during the entire inhalation phase, regardless of respiration volume or rate. In the conserving mode, the conserver immediately delivers oxygen even before inhalation.

In view of the above, it will be seen that the several objects of the invention are achieved and other advantageous results attained.

When introducing elements of the present invention or the preferred embodiment(s) thereof, the articles a, an, the and said are intended to mean that there are one or more of the elements. The terms comprising, including and having are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. A pneumatic oxygen conserver for providing oxygen to a patient, the conserver comprising a body having a cavity therein, a main diaphragm extending across said cavity dividing the cavity into first and second chambers on opposite sides of the main diaphragm, a first inlet passage extending through the body to said first chamber for delivering oxygen from an oxygen supply to said first chamber, a second inlet passage extending through the body to said second chamber for delivering oxygen from the oxygen supply to said second chamber, an outlet passage extending through the body from said first chamber for delivering oxygen from said first chamber to the patient, the main diaphragm being movable between a closed position in which flow of oxygen through the outlet passage is prevented and an open position in which such flow is permitted, vent passaging extending through the body from said second chamber for venting oxygen from said second chamber, a pressure sensitive valve controlling flow through the vent passaging, the valve being operatively connectable to the patient for permitting flow through the vent passaging when the patient inhales and preventing flow through the vent passaging when the patient exhales, valving positioned along said second inlet passage moveable between an open position in which the valving permits flow through said second inlet passage to pressurize said second chamber thereby enabling the conserver to operate in an oxygen conserving mode, and a closed position in which the valving prevents flow through said second inlet passage and vents said second chamber to depressurize said second chamber and prevent further pressurization of said second chamber thereby enabling the conserver to operate in a continuous flow mode, wherein when the valving is in the oxygen conserving mode and the patient inhales the pressure sensitive valve permits flow through the vent passaging to vent said second chamber thereby moving the main diaphragm to its open position for delivering oxygen through the outlet passage to the patient, and when the patient exhales the pressure sensitive valve prevents flow through the vent passaging to pressurize said second chamber thereby moving the main diaphragm to its closed position for preventing flow of oxygen through the outlet passage to the patient, and wherein when the valving is in the continuous flow mode said second chamber vents through the valving thereby causing the main diaphragm to move to its open position to deliver oxygen continuously through the outlet passage to the patient when the patient inhales and exhales.

2. A conserver as set forth in claim 1 wherein said second inlet passage includes an elongate hole extending through the body having an inlet passageway extending into the hole and an outlet passageway extending from the hole at a position longitudinally offset from the inlet passageway, said inlet passageway connecting said oxygen supply to the hole for delivering oxygen to the hole and said outlet passageway connecting the hole to said second chamber for delivering oxygen from the hole to the second chamber.

3. A conserver as set forth in claim 2 wherein said valving includes a valve body moveably positioned in the hole.

4. A conserver as set forth in claim 3 wherein said valve body includes a seal which is selectively positionable along the hole between the inlet passageway and the outlet passageway for blocking flow through the hole from the oxygen supply to the second chamber so the conserver operates in the continuous flow mode.

5. A conserver as set forth in claim 4 wherein the hole has an open end and the outlet passageway is positioned between the open end and the inlet passageway so that when the seal is positioned along the hole between the inlet passageway and the outlet passageway said second chamber continuously vents through the outlet passageway and the open end of the hole thereby depressurizing said second chamber so the second chamber remains at ambient pressure when the patient inhales and exhales causing the main diaphragm to move to its open position so oxygen is continuously delivered through the outlet passage to the patient.

6. A conserver as set forth in claim 5 wherein the seal is positionable along the hole between the outlet passageway and the open end to permit flow from the oxygen supply to the second chamber and prevent flow from the second chamber through the open end of the hole so the conserver operates in the oxygen conserving mode.

7. A conserver as set forth in claim 6 wherein the valve body is slidable within the hole to move the seal between a continuous flow position in which it is positioned between the inlet passageway and the outlet passageway and a conserving flow position in which it is positioned between the outlet passageway and the open end of the hole.

8. A conserver as set forth in claim 7 wherein the valve body is biased so as to move the seal toward the conserving flow position.

9. A conserver as set forth in claim 8 further comprising a mode selector knob rotatably mounted on the body having a cam surface adapted for engaging the valve body to slide the valve body within the hole to selectively move the seal between the conserving flow position and the continuous flow position.

10. A conserver as set forth in claim 2 wherein the inlet passageway includes an orifice for metering flow through said second inlet passage.

11. A conserver as set forth in claim 10 wherein the inlet passageway includes a filter between the oxygen supply and the orifice.

12. A conserver as set forth inc claim 1 in combination with a regulator comprising a regulator body having an inlet adapted for connection to the oxygen supply and an outlet adapted for connection to said first and second inlet passages, and a pressure regulating mechanism in the regulator body operable to receive oxygen from said inlet at a first pressure and to reduce the pressure of the oxygen to a second lower pressure for delivery to said outlet.

13. A pneumatic oxygen conserver for providing oxygen to a patient when the patient inhales, the conserver comprising a body having first and second cavities therein, a main diaphragm extending across said first cavity dividing said first cavity into first and second chambers on opposite sides of the main diaphragm, a first inlet passage extending through the body to said first chamber for delivering oxygen from a supply of oxygen to said first chamber, an outlet passage extending through the body from said first chamber for delivering oxygen from said first chamber to the patient, the main diaphragm being movable between a closed position in which flow of oxygen through the outlet passage is prevented and an open position in which such flow is permitted, a second inlet passage extending through the body to said second chamber for delivering oxygen to said second chamber, sensing diaphragm extending across said second cavity and dividing said second cavity into third and fourth chambers on opposite sides of the sensing diaphragm, a control passage extending through the body connecting said second and third chambers for delivering oxygen from said second chamber to said third chamber, a control orifice positioned along said control passage for restricting flow of oxygen through said control passage, the sensing diaphragm being movable between a closed position in which flow through said control passage is prevented and an open position in which such flow is permitted, a sensing passage extending through the body to the fourth chamber adapted for connection to the patient so pressure in the fourth chamber decreases when the patient inhales and increases when the patient exhales, and a vent passage extending through the body from the third chamber for venting the third chamber, wherein the sensing diaphragm moves to its open position when pressure in said fourth chamber decreases as the patient inhales to vent said second and third chambers and to move the main diaphragm to its open position to deliver oxygen through the outlet passage to the patient, and the sensing diaphragm moves to its closed position when pressure in said fourth chamber increases as the patient exhales to pressurize said second chamber and to move the main diaphragm to its closed position to prevent flow of oxygen to the patient, and wherein the vent passage is sized sufficiently large relative to the control orifice that the sensing diaphragm moves to its closed position in less than about 500 milliseconds after pressure in the fourth chamber approaches about 22 psig as the patient exhales and the vent passage is sized sufficiently small relative to the control orifice that the sensing diaphragm moves to its open position in less than about 500 milliseconds after pressure in the fourth chamber falls below about 22 psig as the patient inhales.

14. A conserver as set forth in claim 13 further comprising a valve positioned along said second inlet passage moveable between an open position to pressurize said second chamber thereby enabling the conserver to operate in an oxygen conserving mode in which oxygen is delivered from said first chamber to the patient when the patient inhales and is prevented from being delivered from said first chamber to the patient when the patient exhales, and a closed position to depressurize said second chamber and prevent further pressurization of said second chamber thereby enabling the conserver to operate in a continuous flow mode in which oxygen is continuously delivered from said first chamber to the patient when the patient inhales and exhales.

15. A conserver as set forth in claim 14 further comprising a metering orifice positioned along said second inlet passage for restricting flow of oxygen through said second inlet passage.

16. A conserver as set forth in claim 13 further comprising a flow control mechanism mounted on the body for selectively varying a flow rate through said outlet passage.

17. A conserver as set forth in claim 16 wherein said flow control mechanism comprises an orifice plate rotatably mounted on the body having a plurality of differently sized orifices therethrough spaced at intervals around the plate, said plate being rotatable within the body to selectively align one of said orifices with said outlet passage to deliver oxygen through said outlet passage at a selected flow rate.

18. A conserver as set forth in claim 13 wherein said main and sensing diaphragms are resiliently flexible and biased toward their closed positions.

19. A conserver as set forth in claim 13 further comprising a spring positioned in the body for biasing the sensing diaphragm toward its closed position.

20. A conserver as set forth in claim 13 wherein said control passage includes a control nozzle positioned in the body so the sensing diaphragm engages the control nozzle when the sensing diaphragm is in its closed position thereby blocking flow through said control passage.

21. A conserver as set forth in claim 20 wherein said control orifice is positioned in the control nozzle.

22. A conserver as set forth in claim 13 wherein said vent passage has a minimum effective flow area which is about 3400 percent of a minimum effective flow area of the control orifice.

23. A conserver as set forth in claim 22 wherein said vent passage has a minimum effective flow area of about 0.0017 square inches and said control orifice has a minimum effective flow area of about 0.00005 square inches.

* * * * *